United States Patent
Hansen et al.

(10) Patent No.: US 8,044,051 B2
(45) Date of Patent: Oct. 25, 2011

(54) METHODS AND COMPOSITIONS FOR THE PRODUCTION OF HIGH CONCENTRATION ALLOXAZINE SOLUTIONS

(75) Inventors: Eric T. Hansen, Thornton, CO (US); Raymond P. Goodrich, Lakewood, CO (US)

(73) Assignee: CaridianBCT Biotechnologies, LLC, Lakewood, CO (US)

( * ) Notice: Subject to any disclaimer, the term of this patent is extended or adjusted under 35 U.S.C. 154(b) by 425 days.

(21) Appl. No.: 11/626,692

(22) Filed: Jan. 24, 2007

(65) Prior Publication Data
US 2007/0178437 A1 Aug. 2, 2007

Related U.S. Application Data

(60) Provisional application No. 60/762,684, filed on Jan. 27, 2006.

(51) Int. Cl.
*A61K 31/525* (2006.01)
(52) U.S. Cl. .............................. 514/251; 435/2
(58) Field of Classification Search .................. 514/251; 435/2
See application file for complete search history.

(56) References Cited

U.S. PATENT DOCUMENTS

| | | | |
|---|---|---|---|
| 2,395,378 A * | 2/1946 | Miller ............................ | 514/161 |
| 2,459,518 A * | 1/1949 | Gerlough et al. ............. | 514/251 |
| 6,258,577 B1 | 7/2001 | Goodrich, Jr. et al. | |
| 6,268,120 B1 | 7/2001 | Platz et al. | |
| 6,277,337 B1 | 8/2001 | Goodrich, Jr. et al. | |
| 6,828,323 B2 | 12/2004 | Platz et al. | |
| 6,843,961 B2 | 1/2005 | Hlavinka et al. | |
| 7,094,378 B1 | 8/2006 | Goodrich et al. | |
| 2002/0015662 A1 | 2/2002 | Hlavinka | |
| 2005/0112021 A1 | 5/2005 | Hlavinka et al. | |

FOREIGN PATENT DOCUMENTS

| WO | WO 02/43485 | 6/2002 |
|---|---|---|
| WO | WO 2004/018471 | 3/2004 |
| WO | WO 2005/014594 | 2/2005 |
| WO | PCT/US2007/002054 | 5/2007 |

OTHER PUBLICATIONS

Selye. The Role Played by the Gastrointestinal Tract in the Absorption and Excretion of Riboflavin. J. Nutr. 1943 25: 137-142.*
Author Unknown, "Introduction," http://www.photobiology.com/v1/rotomskis/intro.htm, 2 pages, at least as early as Aug. 30, 2005.
Author Unknown, "Medical Encyclopedia: Riboflavin," http://www.nlm.nih.gov/medlineplus/print/ency/article/002411.htm, 2 pages, at least as early as Aug. 1, 2005.
Author Unknown, "Photodynamic Therapy," http://www.dermanetwork.com/information/pdt.asp, 2 pages, at least as early as Aug. 30, 2005.
Author Unknown, "Results and Discussion," http://www.photobiology.com/v1/rotomskis/intro.htm, 8 pages, at least as early as Aug. 30, 2005.
Author Unknown, "Solubility," http://chemed.chem.purdue.edu/genchem/topicreview/bp/ch18/soluble.html, 4 pages, at least as early as Aug. 19, 2005.
Author Unknown, "Solubility," http://www.ilpi.com/msds/ref/solubility.html, 2 pages, at least as early as Aug. 19, 2005.
Author Unknown, "Vitamin B2 (Rivoflavin)," http://www.umm.edu/altmed/ConsSupplements/VitaminB2Riboflavincs.html, 9 pages, at least as early as Aug. 1, 2005.
Author Unknown, Sterilization of health care products—Requirements for validation and routine control—Industrial moist heat sterilization, ISO 11134:1994(E), pp. i-iv, 1-22.
Bertolini et al., Role of acetate during platelet storage in a synthetic medium, Transfusion, vol. 32, No. 2, 1992, pp. 152-156.
Braasch, et al., Locked nucleic acid (LNA): fine-tuning the recognition of DNA and RNA, Chemistry & Biology, vol. 8, pp. 1-7, 2001.
Goodrich, et al., The design and development of selective, photoactivated drugs for sterilization of blood products, Drugs of the Future, vol. 22, No. 2, pp. 159-171, 1997.
Murphy, The Oxidation of Exogenously Added Organic Anions by Platelets Facilitates Maintenance of pH During Their Storage for Transfusion at 22°C, Blood, vol. 85, No. 7, pp. 1929-1935, Apr. 1, 1995.
Nielsen et al., Peptide Nucleic Acid (PNA), a DNA Mimic with a Peptide Backbone, Bioconjug.Chem., vol. 5, No. 1, 1994, pp. 3-7.
Sangiorgi, et al., Abnormal platelet mitochondrial function in patients affected by migraine with and without aura, Cephalalgia, vol. 14, pp. 21-23, 1994.
Schoenen, et al., Effectiveness of high-dose riboflavin in migraine prophylaxis, Neurology, vol. 50, pp. 486-470, Feb. 1996.
Uehara, et al., Effect of Adenine on the Riboflavin-sensitized Photoreaction, The Journal of Vitaminology, vol. 17, pp. 148-154, 1971.
Uehara, et al., Effect of Adenine on the Riboflavin-Sensitized Photoreaction, J. Biochem., vol. 71, pp. 805-810, 1972.

* cited by examiner

*Primary Examiner* — Taeyoon Kim
(74) *Attorney, Agent, or Firm* — Laura Butterfield Arciniegas; Edna M. O'Connor; John R. Merkling

(57) ABSTRACT

Methods are provided for preparation of compositions having an enhanced level of soluble alloxazine, as compared to compositions prepared using conventional techniques. Compositions and a riboflavin form having higher solubility in solution is also provided.

3 Claims, 3 Drawing Sheets

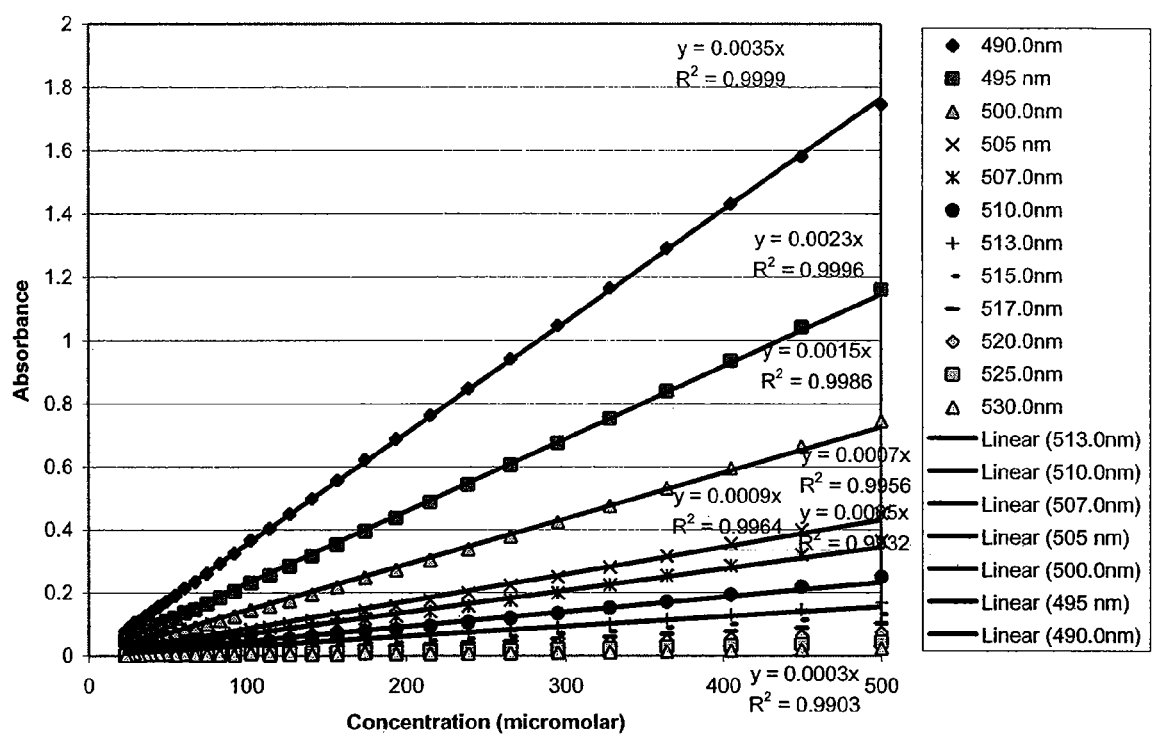
Figure 1A: Riboflavin Absorbance

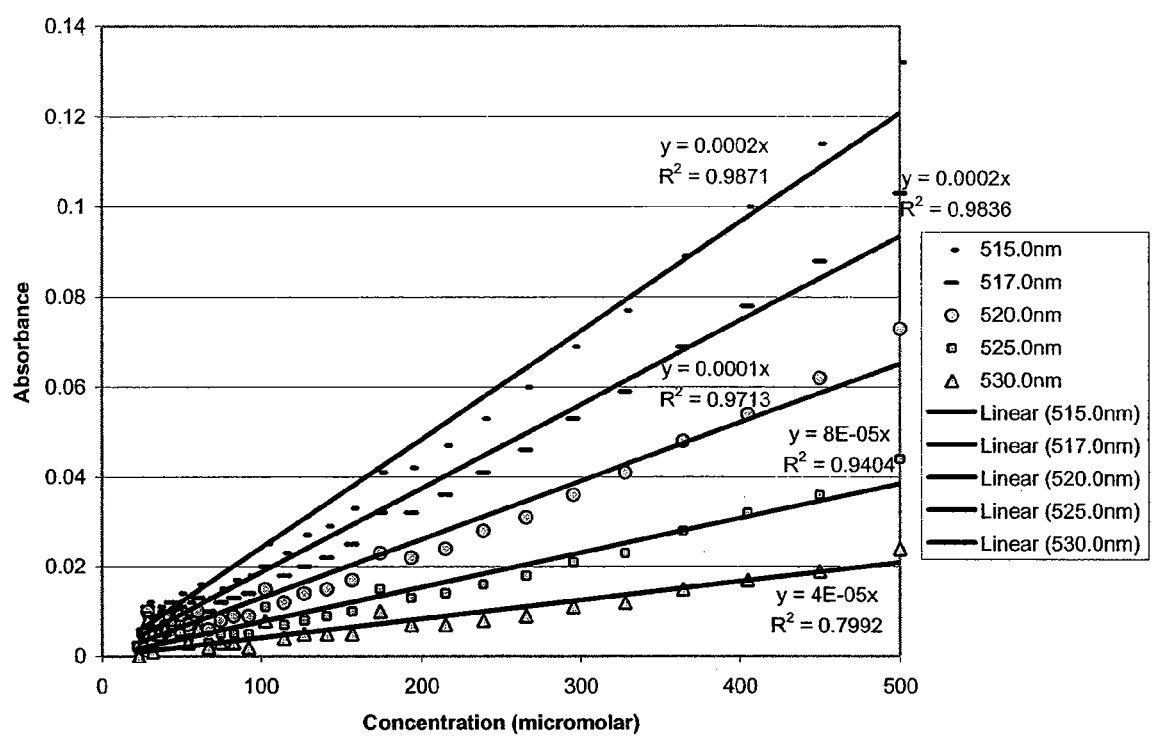
Figure 1B: Riboflavin Absorbance

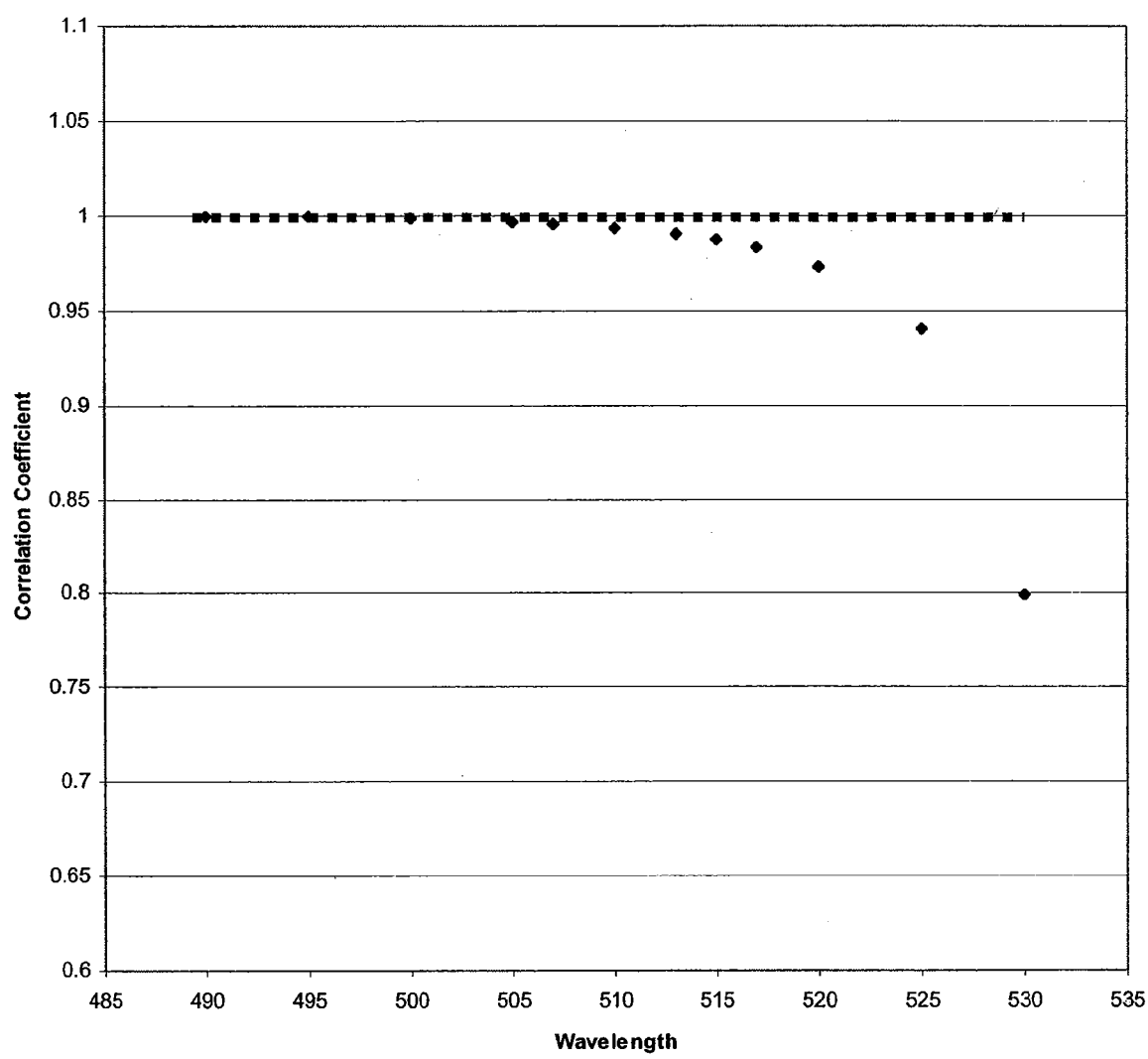
Figure 1C: Linearity Fit vs. Wavelength

METHODS AND COMPOSITIONS FOR THE PRODUCTION OF HIGH CONCENTRATION ALLOXAZINE SOLUTIONS

CROSS-REFERENCE TO RELATED APPLICATIONS

This application claims benefit under 35 U.S.C. §119(e) of U.S. Provisional Application No. 60/762,684 filed Jan. 27, 2006, which is incorporated herein by reference in its entirety.

This application further incorporates the subject matter of U.S. patent application Ser. No. 10/904,361, filed Nov. 5, 2004 and entitled REDUCTION OF CONTAMINATES IN BLOOD AND BLOOD PRODUCTS USING PHOTOSENSITIZERS AND PEAK WAVELENGTHS OF LIGHT, which is incorporated herein by reference in its entirety.

BACKGROUND a. Field

Methods and compositions for increasing the solubility of alloxazines in a solution, as well as inactivating pathogens in biological fluids, are provided. A new form of riboflavin with increased solubility is also provided.

b. Related Art

Contamination of whole blood or blood products with infectious microorganisms such as HIV, hepatitis and other viruses as well as bacteria present a serious health hazard for those who must receive transfusions of whole blood or administration of various blood products or blood components. Such blood components include red blood cells, blood plasma, Factor VIII, plasminogen, fibronectin, anti-thrombin III, cryoprecipitate, human plasma protein fraction, albumin, immune serum globulin, prothrombin complex, plasma growth hormones, and other components isolated from blood.

One solution for providing safe blood or blood products to a recipient is to screen the blood or blood product (herein the terms "blood" and "blood product" are used interchangeably) for contaminates prior to using the material in a patient. When a blood product tests positive for a particular pathogen, the blood product is removed from circulation and destroyed. However, blood screening procedures may fail to detect pathogenic contaminates due to inadequate specificity or sensitivity, for example, a blood product is screened for the presence of hepatitis C, when the blood is infected with West Nile Virus, or the blood product is screened for hepatitis C but the virus is present in an amount below the detection sensitivity of the particular screening methodology. In these situations, the blood screener will leave the blood in circulation noting that it does not contain a detectable level of hepatitis C contamination, where in reality the blood product really has West Nile Virus contamination or a level of hepatitis C contamination that will still damage the health of the recipient.

A second solution for providing a safe blood product to a recipient is to "sterilize" the material prior to use in the recipient. One particularly useful blood product "sterilization" method is to add at least one photosensitizer directly to the blood product. Some types of photosensitizers have a high affinity for nucleic acid. Typically, nucleic acid in a blood product is associated with pathogen presence, allowing the photosensitizer to be preferentially targeted to the pathogen within the blood product. Blood product is then irradiated at an appropriate wavelength, for the photosensitizer, for transfer of the absorbed energy from the photosensitizer to an energy acceptor, i.e., the energy is transferred to the pathogen's nucleic acid. Essentially all pathogens within a blood product be destroyed using this treatment, otherwise, a recipient will receive contaminated blood and be at risk of being infected by the particular pathogen. The amount or level of photosensitizer available within the blood product is a significant aspect of ensuring destruction of pathogens in a sample.

The usefulness of photosensitizer driven destruction of microorganisms is based partly on the amount or concentration of photosensitizer in effective contact with the microorganism, and partly on the "light dose" that reaches those photosensitizers in order to activate the compound and cause killing of the microorganism. In general, the light dose is maximized in order to activate the photosensitizer, but not cause damage to the surrounding blood or fluid products, i.e., erythrocytes, platelets, etc.

However, providing a sufficient amount of photosensitizer to a blood product so as to provide effective killing or inactivation of pathogens in a defined volume of material has proven difficult. In particular, the solubility (measured by its Ksp) of different photosensitizers has limited the amount of photosensitizer that can be added to a blood product. In preparing a photosensitizer for use in a blood product, the solid photosensitizer must first be combined with a solvent to put the material into solution, and then the solution is added to the product at a ratio that does not adversely affect the osmolality of the blood product. This has conventionally provided the limit on how much photosensitizer can be added to a blood product during a "sterilization" treatment.

Dilute quantities of photosensitizers can result in potentially inefficient killing and treatment of pathogens. Therefore, it would be beneficial in the sterilization treatment of blood product to have highly concentrated photosensitizer solutions that are added to the blood product in small amounts and yet provide adequate levels of photosensitizer to the sample to ensure pathogen inactivation. Further, new photosensitizers and forms of photosensitizers are sought after to provide additional tools in the treatment of blood products. New photosensitizers and forms thereof can provide improved energy transfer from the new compound to the blood born pathogen as well as modified solubility characteristics for inclusion with the blood products.

The disclosure has been developed against this backdrop.

SUMMARY

In one aspect, methods for increasing the concentration of an alloxazine in an aqueous medium to above the alloxazine's typical saturation point at ambient temperature and pressure are provided. An aqueous medium having a temperature greater than or equal to 80° C. is added to an amount of alloxazine to form an alloxazine solution exceeding the saturation point of the alloxazine at room temperature (22° C.) and atmospheric pressure (1 atmosphere). The solution is then cooled to produce an aqueous medium having a concentration of alloxazine above the alloxazine's typical saturation point at ambient temperature and pressure.

In various embodiments, the aqueous medium can have an acidic pH (e.g. a pH of from about 4 to about 5), and/or a temperature of between about 80° C. to about 90° C. The aqueous medium can include a salt, such as a monovalent salt. In certain embodiments, the alloxazine is riboflavin. The alloxazine solution can further be sterilized, such as at a pressure of greater than 1 atmosphere and at a temperature of at least 120° C.

In another aspect, a riboflavin derivative form is provided. The riboflavin derivative form has a correlation coefficient equal to or less than 0.95 at a wavelength of 525 nm and/or an absorbance profile as a function of concentration that differs from soluble riboflavin at wavelengths above 500 nm. In further embodiments, the riboflavin derivative form is produced by the process of combining riboflavin in a aqueous medium having an acidic pH and having a temperature of greater than about 80° C., then cooling the riboflavin solution.

In another aspect, compositions for treating a biological fluid, such as a blood product, are provided. In one variation, the composition comprises a soluble alloxazine, such as riboflavin, above the saturation point at 1 atmosphere and 22° C. of at least 120 μM soluble alloxazine, and a monovalent salt. In a further variation, the soluble alloxazine is a concentration of at least 500 μM. In a further variation, the soluble alloxazine is about 580 μM. The monovalent salt can provide a salinity of at least 0.9%. In further variations, the composition can include sodium bicarbonate, and/or can have a pH of from about 4 to about 5.

In other aspects, methods of inactivating pathogens in biological fluids are provided. A composition having a concentration of alloxazine solution is added to the biological fluid to inactivate pathogens. In various embodiments, the concentration of soluble alloxazine is at least 100 μM, 250 μM, at least 500 μM, or about 580 μM. In other embodiments, the biological fluid is a blood product.

BRIEF DESCRIPTION OF THE DRAWINGS

FIGS. 1A, 1B and 1C illustrate the absorbance (Figs A and B) and correlation coefficient (C) characteristics of riboflavin derivative form alpha prepared in accordance with embodiments described herein.

DETAILED DESCRIPTION

Various embodiments provide improved photosensitizer compositions, and in particular improved alloxazine compositions, having increased solubility, and therefore enhanced concentration. The solubility and concentration of the resulting alloxazine solutions are above the solubility and concentration of alloxazines outside of solution. The resulting alloxazine solutions provide a larger quantity of alloxazine to be added to a pathogen-containing biological fluid, resulting in increased pathogen inactivation. A riboflavin derivative form having a higher saturation point than untreated riboflavin is also provided.

Definitions

The following definitions are provided to facilitate understanding of certain terms used frequently herein and are not meant to limit the scope of the present disclosure.

As used herein, "biologic fluid" refers to any fluid(s) found in the body of an animal, and preferably a mammal. Typically, biologic fluids do not have large numbers of materials that contain nucleic acid. For example, a biologic fluid as disclosed herein includes blood products. "Blood product" refers to blood and all blood constituents, blood components and therapeutic protein compositions containing proteins derived from blood.

As used herein, "alloxazine" refers to all alloxazines and isoalloxazines, as well as natural and synthetic derivatives thereof, and includes, but is not limited to: 7,8-dimethyl-10-ribityl isoalloxazine (riboflavin or Vitamin B-2), 7,8,10-trimethylisoalloxazine (lumiflavin), 7,8-dimethylalloxazine (lumichrome), isoalloxazine-adenine dinucleotide (flavin adenine dinucleotide [FAD]), and alloxazine mononucleotide (e.g., flavine mononucleotide [FMN]).

As used herein, "pathogen" refers to an organism that infects and has the potential to cause disease in a host. In particular, pathogens are typically bacterial or viral in nature. As described herein, the terms pathogen and microorganism are interchangeable.

As used herein, the term "inactivation of a pathogen" means partially or completely preventing the pathogen from replicating, either by killing the pathogen or otherwise interfering with the pathogen's ability to reproduce. As used herein, the term "eradicating a pathogen" means completely preventing all pathogens from replicating.

As used herein, "aqueous medium" refers to any medium where the solvent is water.

As used herein, "nucleic acid" ("NA") refers to both a deoxyribonucleic acid (DNA), ribonucleic acid (RNA), and peptide nucleic acid (PNA), as well as modified and/or functionalized versions thereof. Similarly, the term nucleotide as used herein includes individual units of ribonucleic acid and deoxyribonucleic acid as well as nucleoside and nucleotide analogs, and modified nucleotides such as labeled nucleotides. Nucleotide also includes non-naturally occurring analog structures, such as those in which the sugar, phosphate, and/or base units are absent or replaced by other chemical structures. The term nucleotide also includes individual peptide nucleic acid (PNA) units (Nielsen et al., Bioconjug. Chem. (1994) 5(1):3-7) and locked nucleic acid (LNA) units (Braasch and Corey, Chem. Biol. (2001) 8(1):1-7).

As used herein, "peak wavelength" refers to light emitted in a narrow range centered around a wavelength having a particular peak intensity.

As used herein, "solubility" refers to the mass of a substance contained in a solution which is in equilibrium with an excess of the substance. Under these conditions the solution is said to be saturated. The Ksp of a substance is the product of the concentrations of the ions of a substance, in a saturated solution of the substance.

Photosensitizers and Methods of Inactivating Pathogens

Alloxazines are photosensitizers that bind to nucleic acids. Photosensitizers typically bind nonspecifically to nucleic acid molecules and inactivate nucleic acid containing microorganisms by interfering with, and thereby preventing, replication of the organism's nucleic acid. Photosensitizers are activated through illumination with a specific wavelength of light, specific for the photosensitizer, which causes an energy transfer from the photosensitizer to an energy acceptor, e.g., a nucleic acid base pair. In general, photosensitizer specificity is based on close proximity of the photosensitizer to the microorganism's nucleic acid, which results in binding of the photosensitizer to the pathogen's nucleic acid.

Photosensitizers are most useful when the biologic fluid to be treated is devoid, or has limited numbers, of non-pathogenic nucleic acid molecules, i.e., when the nucleic acid present in a biological fluid is due primarily to a pathogen's presence, and not due to other cells within the same sample. So, for example, a typical treatment process of a biologic fluid includes addition of the photosensitizer to a blood product potentially contaminated with a pathogenic organism.

If pathogen reduction of blood and/or blood components is desired, additives which act as photosensitizers upon exposure to light can be used in conjunction with the methods, compounds, and compositions described herein. Such additives include endogenous photosensitizers. The term "endogenous" means naturally found in a human or mammalian body, either as a result of synthesis by the body or because of ingestion as an essential foodstuff (e.g. vitamins) or formation of metabolites and/or byproducts in vivo.

Examples of such endogenous photosensitizers are alloxazines such as 7,8-dimethyl-10-ribityl isoalloxazine (riboflavin), 7,8,10-trimethylisoalloxazine (lumiflavin), 7,8-dimethylalloxazine (lumichrome), isoalloxazine-adenine dinucleotide (flavin adenine dinucleotide [FAD]), alloxazine mononucleotide (also known as flavin mononucleotide [FMN] and riboflavin-5-phosphate), their metabolites and precursors. The term "alloxazine" includes isoalloxazines. Endogenously-based derivative photosensitizers include synthetically derived analogs and homologs of endogenous photosensitizers which may have or lack lower (1-5) alkyl or halogen substituents of the photosensitizers from which they are derived, and which preserve the function and substantial non-toxicity thereof. When endogenous photosensitizers are used, particularly when such photosensitizers are not inherently toxic or do not yield toxic photoproducts after photoradiation, no removal or purification step is required after decontamination, and treated product can be directly returned to a patient's body or administered to a patient in need of its therapeutic effect.

When photosensitizers are exposed to light of a particular wavelength, they absorb energy resulting in the photolysis of the photosensitizer and any nucleic acid bound to the photosensitizer. Efficacy of the photosensitizer depends on both the concentration of the photosensitizer incorporated by the pathogen and on the illumination dose (since the excited photosensitizer is the active agent in destroying the pathogen). In general, a photochemical dose, therefore, is equal to the concentration of the photosensitizer added to the fluid and the light dose.

The light dose is based on providing maximal destruction to pathogenic organisms without adversely affecting the biological fluid of interest. Peak wavelength, as defined herein, refers to light emitted in a narrow range centered around a wavelength having a particular peak intensity. In one embodiment, visible light may be centered around a wavelength of approximately 470 nm, and have maximal intensity at approximately 200 nm to about 550 nm. In an alternative embodiment, the light may be centered around 308 nm, and have maximal intensity at approximately 280 nm to about 370 nm. Note that the term "light source" or "radiation" refers to an emitter of radiant energy, and may include energy in the visible and/or ultraviolet range. As noted above, it is difficult to improve a photosensitizer dose within a target fluid by altering the light dose, as a stronger or more efficient light dose will likely adversely affect the stability of other constituents within the fluid, i.e., lyse erythrocytes within a blood product sample.

As has been previously described in U.S. patent Publication 20050112021 (Hlavinka et al., May 26, 2005), incorporated herein by reference, photosensitizer is added to target fluids, and the resulting fluid mixture exposed to photoradiation of the appropriate peak wavelength and amount to activate the photosensitizer, but less than that which would cause significant non-specific damage to the biological components or substantially interfere with biological activity of other proteins present in the fluid.

Pathogens can be inactivated or eradicated by adding a solution or composition having at least 120 μM soluble alloxazine to a biological fluid. The solutions or compositions can be adjusted to desired alloxazine concentrations above the untreated concentration at 1 atmosphere and 22° C. by the methods described herein. The increased solubility and concentration of the alloxazine solutions allows a larger quantity of alloxazine to be added to pathogen-containing biological fluids. This results in increased pathogen inactivation.

Microorganisms which may be eradicated or inactivated using photosensitizers as described herein include, but are not limited to, viruses (both extracellular and intracellular), bacteria, bacteriophages, fungi, blood-transmitted parasites, and protozoa. Illustrative viruses include human acquired immunodeficiency virus (HIV), hepatitis A, hepatitis B, hepatitis C, sinbis virus, cytomegalovirus, vesicular stomatitis virus, herpes simplex virus (Type I and Type II), West nile virus, human T-lymphotropic retroviruses, HTLV-III, lymphadenopathy virus LAV/IDAV, parvovirus, transfusion-transmitted (TT) virus, Epstein-Barr virus, as the like. Bacteriophages which may be eradicated or inactivated using photosensitizers, include, but are not limited to .PHI.X174, .PHI.6, lambda bacteriophage, R17, $T_4$, $T_2$ and the like. Bacteria which may be eradicated using photosensitizers, include, but are not limited to, *P. aeruginosa, S. aureus, S. epidermis, L. monocytogenes, Escherichia coli, K. pneumonia, S. marcescens* and the like.

Methods of Preparing Alloxazine Compositions

Methods for increasing the concentration of an alloxazine in an aqueous medium to above the alloxazine's ordinary saturation point are also provided. In one embodiment, an amount of an alloxazine that exceeds the saturation point of the alloxazine is added to an aqueous medium that has a temperature greater than or equal to 80° C. When the solution is cooled, the alloxazine in the resulting alloxazine solution exceeds the saturation point of the alloxazine. The alloxazine can be added to the aqueous medium before or while the medium is heated. The alloxazines are stable in solution over time, and are not super-saturated in the aqueous solution.

Alloxazines can be purchased commercially. Crystalline alloxazine, e.g., riboflavin (7,8-dimethyl-10-ribityl isoalloxazine), FMN, FAD, lumichrome, etc, regardless of the particular form, can be obtained from Merck, see for example The Merck Index, $10^{th}$ edition, 1983.

An amount of alloxazine is measured for combination with a solvent such as an aqueous medium or a combination of aqueous medium and a non-polar solvent. For example, the saturation point concentration of the alloxazine riboflavin at 22° C. and 1 atmosphere pressure was measured to be 114 μM. The concentration of the alloxazine prepared by the methods described herein is significantly higher than the original dissolved concentration. The final alloxazine concentration can be targeted to be equal to and/or greater than 120 μM, 150 μM, 200 μM, 250 μM, 300 μM, 350 μM, 400 μM, 450 μM, 500 μM, 550 μM, 580 μM, 600 μM, or 650 μM. In certain embodiments, the concentration of alloxazine is targeted to be approximately 500 μM±12.5 μM.

The pH of the solvent also can be adjusted. For example, the pH can be adjusted to an acidic pH (i.e. less than or equal to 6.5). The solvent pH can be modified to be less than or equal to a maximum pH of 6.5, 6.0, 5.5, 5.0, 4.5, 4.0, 3.5, 3.0 or 2.5, and optionally greater than or equal to a minimum pH of 2.5, 3.0, 3.5, 4.0, 4.5. 5.0. 5.5, or 6.0. For example, the pH can be modified to between 4.0 and 5.0. Any acid can be used to modify the pH, including for example, hydrochloric acid (HCl), sulfuric acid ($H_2SO_4$), citric acid ($C_6H_8O_7$) and acetic acid ($CH_3COOH$). Common bases can also be used to modify the pH, including sodium hydroxide (NaOH) and sodium bicarbonate ($NaHCO_3$).

A monovalent salt, e.g., NaCl, can be combined with the solvent to provide a salinity of about 0.9%. In addition, the solution can be prepared to include about 200 mM sodium acetate (NaAc). The sodium acetate is typically included for end-use in blood products, where 10-20 mM NaAc is used within the blood product for platelet stability and activity Bertulini et al., Transfusion (1992) 32:152; Murphy, Blood (1995) 85:1929. As above, the NaAc can be added with the alloxazine and salt of independent of the alloxazine and salt. The order of addition is not critical to the production of the alloxazine containing solvent.

Under conventional alloxazine solution production, only about the equivalent of a 114 µM solution will be produced due to the materials marginal solubility. i.e., Ksp. The concentration of the alloxazine can be targeted to a specific level higher than the typical saturation concentration, as discussed supra.

The aqueous medium is heated to a given temperature. For example, the aqueous medium can be heated to a minimum temperature of greater than or equal to 60° C., 65° C., 70° C., 75° C., 80° C., 85° C., 90° C., or 95° C., and optionally a maximum temperature of less than or equal to 95° C., 90° C., 85° C., 80° C., 75° C., 70° C., or 65° C. In certain variations, the temperature of between about 80° C. to about 90° C. The solution can be mixed for a period of time, such as for at least ten to sixty minutes, to allow the alloxazine to dissolve.

Heated and mixed solution is then autoclaved in flexible plastic bags, or other like containers, under enhanced steam, pressure and temperature. No volume constraints are placed on the solution. In particular, the solution is heated to between about 60° C. and about 100° C., and preferably about 75° C. to about 85° C., and a pressure of between about 1 atm and about 4 atm (50 psi), under high steam conditions.

The compositions can be stored for later use. For example, sodium acetate can be added to the composition. The composition can be dispensed into sterilization vessels, for example, polypropylene bags, which can then be heated (to e.g. 120° C.-130° C.) for an appropriate period of time and steam sterilizing the composition in a light-occluded manner.

The alloxazine solutions prepared in this manner can be used in the treatment of biologic fluids and such as blood products. Alloxazine containing solutions have enhanced solubility and stability as compared to alloxazine solutions not prepared using the methods described herein.

The compositions, as prepared by methods described herein, are then added directly to the biological fluid, such as a blood product. In certain embodiments, approximately 35 ml of 500 µM alloxazine solution is added per 170 ml to 365 ml blood product. The addition of the alloxazine composition to the blood product is in distinct comparison to previous technologies, which require a much more dilute combination of alloxazine into the blood product.

Riboflavin Derivative Forms

The method of preparing the riboflavin by heating and then cooling in solution creates a riboflavin derivative form that has increased solubility at room temperature as compared to untreated riboflavin. The compound has been termed riboflavin derivative alpha. Riboflavin derivative alpha can be used as in the sterilization treatment of biological fluids.

Riboflavin derivative alpha is a highly soluble form of riboflavin created by heating under acidic conditions. The chemical structure and activity of the riboflavin derivative form is the same as that of untreated riboflavin. Without being limited to a specific theory, the riboflavin derivative form appears to be an altered conformation of riboflavin that excludes water from the hydration sphere. Such a conformational change allows the riboflavin to act as an organic solvent, thereby allowing increased solubility of riboflavin in solution. The spectroscopic data is consistent with solubilizing riboflavin in a more hydrophobic environment. Riboflavin derivative alpha is stable over time, and is not a supersaturated solution.

At least some portion of the riboflavin material derived from the methods described herein contain riboflavin derivative alpha. Riboflavin derivative alpha can be present exclusively or as part of a combination of riboflavin or with other alloxazine compounds. The compound is highly stable at room temperature and can be stored for extended periods of time, while retaining high activity for use in the treatment of biologic fluids. As shown below in the Examples, riboflavin derivative alpha provides an altered or modified absorbance profile as a function of concentration at wavelengths above 500 nm.

A modified absorbance profile for riboflavin derivative alpha, as compared to untreated riboflavin, indicates that this new derivative of riboflavin is present (see Beer's law, $A=\epsilon bc$, where A is absorbance, $\epsilon$ is the molar absorptivity, b is the path length of the sample, i.e., cuvette and c is the concentration of the compound in solution).

The methods, compositions and devices disclosed herein may also be used to make vaccines, reduce prions in a fluid, in IV fluids containing biologically active proteins other than those derived from blood may also be treated by the methods, compounds and compositions described herein.

EXAMPLES

The present disclosure will be more readily understood by reference to the following examples, which are provided by way of illustration and are not intended as limiting.

Example: 1

Batch Manufacture of Highly Soluble Riboflavin

Procedure for Compounding of Bulk Solution:

The following procedure is performed in a clean room. For a given desired bulk volume of manufactured riboflavin solution, enough solid riboflavin and sodium chloride are measured and dispensed into a tank filled with 80° C. water to produce a solution having 500 µM±12.5 µM riboflavin and approximately 153.6 mM±3.6 mM. In particular, a 1000 L batch would consist of 0.1882 kg riboflavin and 9.0 kg sodium chloride. Note that the riboflavin and sodium chloride can be added simultaneously or individually in either order of addition.

More particularly, the sodium chloride is added to the WFI (injection quality water or "water for injection") WFI is at a temperature of 80° C., and the pH adjusted with 0.1M HCl to 5.0±0.1. The riboflavin is then added and the solution and mixed for about 15 minutes. Again note that the order of addition between the sodium chloride and riboflavin is irrelevant. The temperature of the solution is maintained at about 80° C. A quality control analysis was performed to determine purity of the composition.

Procedure for Filing Bags and Steam Sterilization:

The above solution was then filtered through a Durapore 10" 0.45 µm in-line filter. The filtered bulk solution is next transferred to a filling machine where the solution is dispensed into 35 ml labeled PVC bags. The bags were then wrapped in a polypropylene vacuum overwrap prior to steam sterilization using an overkill method.

The overkill method was performed pursuant to ISO 11134:1994, entitled Sterilization of heath care products—Requirements for validation and routine control—Industrial moist heat sterilization. The ISO provides a guideline for the preparation of medical products using steam sterilization techniques.

The sterilization cycle includes heating the solution to 121° C. for approximately 15 minutes at a pressure of 4 atm in the polypropylene bags. The bags were then steam sterilized by placing them in a labeled foil pouch to prevent light exposure to the solution (avoids photodegradation of riboflavin). A sample was then tested using a finished goods test—the sample complied with the following parameters: riboflavin, 500±25 µM; lumichrome, <75 µM; sodium chloride, 154±7 mM; sub visible particles, >10 µm (6000/container), >25 µm (600/container); pH, 4.0-5.1; endotoxins, <0.5 EU/ml; and sterility, <10-6 (sterility assurance level (SAL) for fluid pathway).

Example 2

Riboflavin Derivative Alpha

The riboflavin derivative, termed riboflavin alpha was prepared using the procedures described above in Example 1. To confirm that the material contained riboflavin, the composition was tested for absorbance at 2 nm to 5 nm intervals between the wavelengths of 490 nm and 530 nm. Absorbance numbers were then entered into Beer's law ($A=\epsilon bc$) where A is absorbance, $\epsilon$ is the molar absorptivity for riboflavin, b is the path length of the sample, i.e., cuvette and c is the concentration of the compound in solution. Concentration was solved for at each absorbance and plotted as shown in FIGS. 1A, 1B and 1C. The slope of the line of Absorbance versus concentration equals the molar absorptivity ($\epsilon$).

Interestingly, when the data from FIG. 1C was measured for its correlation coefficient, i.e., concentration plotted for each wavelength and a correlation coefficient prepared, a substantial deviation was identified for wavelengths above 500 nm, and particularly at 510 nm. The data in FIG. 1C illustrates that a distinct riboflavin derivative form exists in the tested composition, which is therefore prepared using the methods described herein. This derivative has been termed riboflavin derivative alpha.

Example 3

Riboflavin (approximately 70 mg) was added to saline (approximately 200 mL) and continuously mixed on a hot plate. The container was covered, and the solution was mixed for 40 minutes. the solution was filtered through a 0.2 micron filter. The filtered solution was diluted 1:10 and its absorbance was measured. The riboflavin concentration was determined to be 540 µM. The spectrum showed no evidence of riboflavin decomposition.

3 mL of the riboflavin and 147 mL saline were combined. The absorbance was measured, and the concentration was determined to be 9.9 µM. 30 mL of the riboflavin/saline solution was transferred to each of four 75 cm² flasks, which were irradiated two at a time.

The concentrations of riboflavin solutions were determined to be 515 µM and 528 µM, above the 114 µM concentration of untreated riboflavin dissolved into solution at ambient temperature and pressure.

Example 4

The concentration stability of riboflavin was measured over a period of time to determine its stability.

Various preparation of riboflavin were prepared.

Riboflavin was dissolved in aqueous medium at 22° C., and its concentration was measured at 114 µM.

Samples 1-3 were prepared by adding 10 mg riboflavin to 100 mL saline, heating at 37° C. for 30 minutes, mixing on a stir-plate for 20 minutes, and filtering through a 20 micron filter.

Sample 4 was made by adding 10 mg riboflavin to 100 mL saline, heating, and filtering through a 0.2 micron filter.

Sample 5 was prepared by adding 20 mg riboflavin to 100 mL saline, heating while mixing for 30 minutes, and filtering through a 0.2 micron filter.

Sample 6 was prepared by adding 5 mg riboflavin to 10 mL saline, heating in a water bath at 60° C. for 30 minutes, shaking vigorously for 30 seconds, and filtering through a 0.2 micron filter.

The concentration stability of riboflavin compositions are shown for each preparation. The riboflavin concentration of each experimental heat treated riboflavin sample is above that of the unheated control sample. Further, the concentration remains stable over a period of time when stored at ambient temperature and pressure.

TABLE 1

| Sample | Riboflavin Concentration Day 0 (µM) | Riboflavin Concentration Day 5 (µM) |
| --- | --- | --- |
| Control | 114 | 114 |
| 1 | 154 | 153 |
| 2 | 149 | 146 |
| 3 | 144 | 144 |
| 4 | 217 | 218 |
| 5 | 389 | 352 |
| 6 | 473 | not measured |

It is understood for purposes of this disclosure that various changes and modifications may be made to the invention that are well within the scope of the invention. Numerous other changes may be made which will readily suggest themselves to those skilled in the art and which are encompassed in the spirit of the methods, compounds and compositions disclosed herein.

The specification contains numerous citations to patents, patent applications, and publications, each is hereby incorporated by reference for all purposes.

We claim:

1. A method of increasing the concentration of an alloxazine in an aqueous medium consisting of sodium chloride to above the alloxazine's saturation point, the method comprising:

adding an amount of said alloxazine to an aqueous medium consisting of about 0.9% sodium chloride at a pH of between about 4 and about 5, wherein the amount of alloxazine exceeds the saturation point of said alloxazine at 1 atmosphere and 22° C:

heating said aqueous medium consisting of sodium chloride and alloxazine to a temperature between about 80° C. and about 90° C; and cooling said aqueous medium consisting of sodium chloride and alloxazine to produce an aqueous medium having a concentration of alloxazine above the alloxazine saturation point.

2. The method of claim 1, wherein the alloxazine is riboflavin.

3. The method of claim 1, further comprising sterilizing the aqueous medium consisting of sodium chloride and alloxazine after cooling under pressure at a temperature of at least 120° C.

* * * * *